United States Patent [19]

Hirai et al.

[11] Patent Number: 5,053,557

[45] Date of Patent: Oct. 1, 1991

[54] PROCESS FOR PREPARING 2-CHLORO-4-FLUOROPHENOL

[75] Inventors: Kenji Hirai; Mitsuo Yamashita, both of Kanagawa, Japan

[73] Assignee: Sagami Chemical Research Center, Tokyo, Japan

[21] Appl. No.: 578,242

[22] Filed: Sep. 6, 1990

[30] Foreign Application Priority Data

Sep. 12, 1989 [JP] Japan .................................. 1-234774

[51] Int. Cl.$^5$ ....................... C07C 39/27; C07C 37/62
[52] U.S. Cl. .................................. 568/775; 568/779
[58] Field of Search ............... 568/775, 779, 776, 774, 568/775

[56] References Cited

U.S. PATENT DOCUMENTS 3,929,907 12/1975 Janzon et al. ....................... 568/775
4,620,042 10/1986 Kawai et al. ....................... 568/775

FOREIGN PATENT DOCUMENTS 25344 2/1984 Japan ................................. 568/775
154249 9/1963 U.S.S.R. ............................. 568/775
2155468 3/1984 United Kingdom ................. 568/775

Primary Examiner—Werren B. Lone
Attorney, Agent, or Firm—Nixon & Vanderhye

[57] ABSTRACT

A process is disclosed for preparing 2-chloro-4-fluorophenol which comprises chlorinating 4-fluorophenol with a chlorinating agent in the presence of water. The process according to the present invention has advantages in that the chlorination can be carried out using inexpensive reagents without requiring the use of particular apparatus and under mild conditions, and the desired product can be obtained in good yields and with high selectivity. 2-Chloro-4-fluorophenol obtained in the present invention is useful as a starting material for producing various pharmaceutical agents and agricultural agents.

9 Claims, No Drawings

PROCESS FOR PREPARING 2-CHLORO-4-FLUOROPHENOL

FIELD OF THE INVENTION

This invention relates to a process for preparing 2-chloro-4-fluorophenol which comprises chlorinating 4-fluorophenol in the presence of water.

BACKGROUND OF THE INVENTION

2-Chloro-4-fluorophenol is an important intermediate for producing various pharmaceutical and agricultural agents. For example, oxazolidine derivatives derived from 2-chloro-4-fluorophenol possess an excellent herbicidal activity as disclosed in Japanese Patent Public Disclosure (Kokai) No. 62-174065 which corresponds to U.S. Pat. No. 4,818,272 and Japanese Patent Public Disclosure (Kokai) No. 62-167713 which corresponds to EP 241,559.

Typical conventional processes for preparing 2-chloro-4-fluorophenol include (1) a process comprising nitrating 4-fluoroanisol as a starting compound, followed by reducing the nitro group, converting the resulting compound into 2-chloro-4-fluoroanisol by the Sandmeyer reaction, and cleaving the ether linkage of the resulting compound, as disclosed in J. Am. Chem. Soc., 81, 94 (1959), and (2) a process comprising directly introducing a chlorine atom into 4-fluorophenol as a starting material using various chlorinating agents.

The above conventional process (1) makes it possible to selectively introduce a chlorine atom into the 2-position of 4-fluorophenol, but is not advantageous on an industrial scale since the process involves a number of reaction steps. Also, the above conventional process (2) can be carried out by one of various chlorinating procedures depending upon the type of the chlorinating agent used. For example, the process (2) includes (i) chlorination of 4-fluorophenol or an alkali metal thereof using an alkali metal hypochlorite as disclosed in USSR Patent No. 154250 and Zh. Obshch. Khim., 37, 2486 (1967), (ii) chlorination using sulfuryl chloride in the presence of a base as disclosed in Japanese Patent Public Disclosure (Kokai) No. 59-25344, (iii) chlorination using hydrochloric acid and hydrogen peroxide under an acidic condition as disclosed in Japanese Patent Public Disclosure (Kokai) Nos. 62-223140 and 62-238226, and (iv) direct chlorination using chlorine gas as disclosed in Japanese Patent Publication No. 63-62497 which corresponds to U.S. Pat. No. 4,620,042.

However, the above-described process (i) to (iv) also have various disadvantages. More specifically, the process (i) is not advantageous in that a highly concentrated aqueous solution of alkali metal hypochlorite is not available and, thus, the reaction should be conducted in an aqueous solution of alkali metal hypochlorite having a low concentration thereby resulting in a low space factor and a low yield, e.g., approximately 80%. The process (ii) exhibits a high position-selectivity, but produces as by products, hazardous waste gases such as sulfurous acid gas and hydrogen chloride gas which must be treated. The process (iii) requires the use of hydrogen peroxide which cannot be handled easily and, further, produces a waste sulfuric acid solution which must be treated. Although the process (iv) is an effective chlorination process, it requires separation of hydrogen chloride gas having a boiling point of $-85°$ C. produced during the reaction from chlorine gas having a boiling point of $-34.1°$ C. using a highly efficient refluxing condenser during the reaction in order to obtain an improved selectivity. In the separation of gases having such low boiling point, it is necessary to use a cooling tube which is effective at temperatures below the boiling point of chlorine gas and such a cooling means consumes large quantities of electricity. Also, the process (iv) produces, similar to the process (ii) described above, hydrogen chloride waste gas which must be treated. Further, the reaction of the process (iv) is not viable on an industrial scale since it gives rise to a remarkable decrease in selectivity even when a very small amount of impurities, in particular, metal ions, is present in the reaction system, and, hence, the reaction vessel used must be carefully selected from those made of a material which does not produce such impurities during the reaction.

As a result of extensive studies for developing a process which is viable on an industrial scale, which is capable of producing the desired 2-chloro-4-fluorophenol in good yields and with high selectivity, and which can be carried out under mild reaction conditions using inexpensive reagents without necessitating the use of particular apparatus, the present inventors found that 2-chloro-4-fluorophenol can be prepared in good yields and with high selectivity by directly chlorinating 4-fluorophenol with an inexpensive chlorinating agent such as chlorine gas or sulfuryl chloride in the presence of water.

DETAILED DESCRIPTION OF THE INVENTION

The characteristic feature of the process according to the present invention resides in that the chlorination reaction is conducted in the presence of water. Water used in the reaction includes not only substantially pure water but also an aqueous solution containing an inorganic salt such as sodium chloride, magnesium chloride, etc., or an acid such as acetic acid, hydrochloric acid, etc. If desired, a solvent which does not adversely affect the reaction such as carbon tetrachloride, chloroform, dichloromethane, dichloroethane, etc. can be used in the reaction in combination.

In the process according to the present invention, the chlorination reaction is performed in a two-layer reaction system due to the presence of water. That is, the chlorination reaction proceeds in an organic layer, and hydrogen chloride generated in the reaction is completely transferred into an aqueous layer thereby preventing a decrease in position-selectivity during the chlorination process. Thus, the process of the present invention is remarkably different from the conventional process described above. Accordingly, the process of the present invention does not require the use of any particular apparatus such as a cooling tube and can be carried out sufficiently in a usual reaction apparatus. Further, a small amount of impurities such as metal ions can be trapped in the aqueous layer, and, hence, a reactor which is expected to dissolve out metal ions during the reaction under an acidic condition can be used without adversely affecting the reaction.

In the present invention, the amount of water used is not limited, and the reaction proceeds with high selectivity and without any problem in the presence of water in an amount sufficient to dissolve all of the hydrogen chloride generated during the reaction.

In the process of this invention, the chlorinating agent can be generally used in an amount of from 0.1 to 3 mols per mol of 4-fluorophenol. In particular, production of highly chlorinated by-products can be minimized when chlorine gas as a chlorinating agent is used in an amount of from 0.8 to 1.2 mol per mol of 4-fluorophenol or when sulfuryl chloride as a chlorinating agent is used in an amount of from 1.6 to 2.2 mol per mol of 4-fluorophenol. Also, when the reaction is conducted using a chlorinating agent in an amount below the required amount, the desired product can be produced in an amount approximately in proportion to the amount of the chlorinating agent used.

The reaction temperature is not particularly limited and the reaction proceeds sufficiently at temperatures which can be produced without utilizing a cooling means such as a cooling tube. However, it is preferable to conduct the reaction at a temperature of from 0° to 80° C. since, at such a temperature, the reaction be completed within a short period of time and the desired product can be obtained in good yields with high selectivity. Further, since the reaction of the present invention is a two-layer system reaction, it can be conducted in the presence of a phase transfer catalyst such as a tertiary ammonium salt. Examples of the tertiary ammonium salt include benzyltriethylammonium chloride, tetraethylammonium chloride, tetrabutyl ammonium hydroxide, etc.

The present invention is further illustrated in more detail by the following Examples, but the present invention is not limited thereto.

EXAMPLE 1

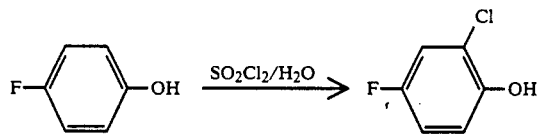

4-Fluorophenol (11.2 g, 0.10 mol) and water (20 ml) were placed in a 200 cc three-necked glass flask equipped with a stirrer and a dropping funnel, and sulfuryl chloride (15 ml, 25.2 g, 0.19 mol) was added dropwise thereto over a period of 25 minutes while maintaining the reaction solution at 60° to 70° C. After completion of the reaction, a saturated aqueous solution of sodium chloride (200 ml) was added to the reaction solution which was then extracted with dichloromethane (100 ml×3). The organic layer was dried over anhydrous magnesium sulfate. The drying agent was removed, and the solvent was distilled off under reduced pressure to obtain a crude product (13.3 g). The composition of the product was found to be 2-chloro-4-fluorophenol (94.8%), 2,6-dichloro-4-fluorophenol (2.7%) and unreacted starting material (2.5%) (by glc), and production of other highly chlorinated products was not observed.

EXAMPLE 2

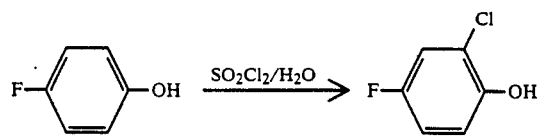

4-Fluorophenol (44.8 g, 0.40 mol) and water (80 ml) were placed in a 500 cc three-necked glass flask equipped with a stirrer and a dropping funnel, and sulfuryl chloride (60 ml, 100 g, 0.74 mol) was added dropwise thereto over a period of 60 minutes while maintaining the reaction solution at 60° to 70° C. After completion of the reaction, a saturated aqueous solution of sodium chloride (400 ml) was added to the reaction solution which was then extracted with dichloromethane (200 ml×3). The organic layer was dried over anhydrous magnesium sulfate. The drying agent was removed, and the solvent was distilled off under reduced pressure to obtain a crude product (56.4 g). The composition of the product was found to be 2-chloro-4-fluorophenol (98.3%), 2,6-dichloro-4-fluorophenol (1.0%) and unreacted starting material (0.7%) (by glc), and production of other highly chlorinated products was not observed.

EXAMPLE 3

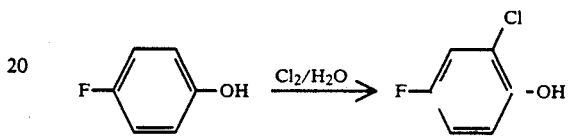

4-Fluorophenol (11.2 g, 0.10 mol) and water (20 ml) were added to a three-necked glass flask equipped with a chlorine-gas introducing tube, and an equimolar amount of chlorine gas was introducing into the mixture at 5° C. over a period of 15 minutes. After completion of the reaction, the aqueous layer and the organic layer were separated to obtain a crude product. The composition of the product was found to be 2-chloro-4-fluorophenol (93.4%), 2,6-dichloro-4-fluorophenol (6.5%) and unreacted starting material (0.1%) (by glc), and production of other highly chlorinated products was not observed. Dichloromethane (100 ml) was then added to the product, and the organic layer was washed with a saturated aqueous solution of sodium chloride (50 ml×3) and dried over anhydrous magnesium sulfate (50 ml×3). The drying agent was removed, and the solvent was distilled off under reduced pressure to obtain 2-chloro-4-fluorophenol as a pale brown solid (14.4 g).

EXAMPLE 4

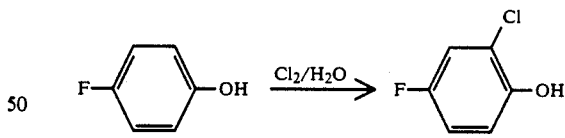

4-Fluorophenol (11.2 g, 0.10 ml) and water (20 ml) were added to a 200 cc stainless steel vessel equipped with a chlorine-gas introducing tube, and an equimolar amount of chlorine gas was introduced into the mixture at 60° C. over a period of 30 minutes. After completion of the reaction, the aqueous layer and the organic layer were separated to obtain a crude product. The composition of the produce was found to be 2-chloro-4-fluorophenol (92.3%), 2,6-dichloro-4-fluorophenol (5.8%) and unreacted starting material (1.9%) (by glc), and production of other highly chlorinated products was not observed. The resulting organic layer was dissolved in dichloromethane (300 ml), and the solution was washed with a saturated aqueous solution of sodium chloride (100 ml) and dried over anhydrous magnesium sulfate. The drying agent was removed, and the solvent was distilled off under reduced pressure to obtain 2-chloro-4-fluorophenol as a pale brown solid (13.8 g).

EXAMPLE 5

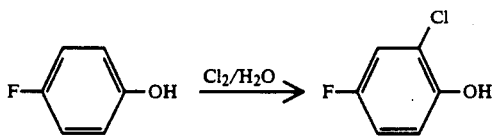

4-Fluorophenol (11.2 g, 0.10 mol), benzyltriethylammonium chloride (0.1 g), chloroform (50 ml) and water (20 ml) were added to a 200 cc three-necked glass flask equipped with a chlorine-gas introducing tube, and an equimolar amount of chlorine gas was introduced into the mixture at 60° C. over a period of 40 minutes. The aqueous layer and the organic layer were separated, and the organic layer was dried with anhydrous magnesium sulfate. The drying agent was removed, and the solvent was distilled off under reduced pressure to obtain a crude product. The composition of the product was found to be 2-chloro-4-fluorophenol (90.2%), 2,6-dichloro-4-fluorophenol (6.1%) and unreacted starting material (3.7%) (by glc), and production of other highly chlorinated products was not observed.

EXAMPLE 6

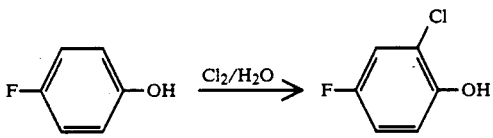

4-Fluorophenol (11.2 g, 0.10 mol), benzyltriethylammonium chloride (0.1 g) and water (20 ml) were added to a 200 cc three-necked glass flask equipped with a chlorine-gas introducing tube, and an equimolar amount of chlorine gas was introduced into the mixture at 60° to 70° C. over a period of 15 minutes. After completion of the reaction, the aqueous layer and the organic layer were separated to obtain a crude product. The composition of the product was found to be 2-chloro-4-fluorophenol (92.2%), 2,6-dichloro-4-fluorophenol (5.2%) and unreacted starting material (2.6%) (by glc), and production of other highly chlorinated products was not observed.

EXAMPLE 7

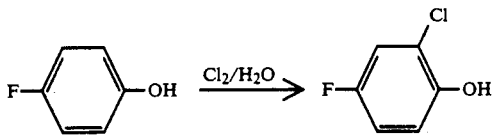

4-Fluorophenol (11.2 g, 0.10 mol) and dichloromethane (20 ml) were added to a 200 cc three-necked glass flask equipped with a chlorine-gas introducing tube, and an equimolar amount of chlorine gas was introduced into the mixture at 15° C. over a period of 20 minutes. After completion of the reaction, the aqueous layer and the organic layer were separated, and the organic layer was dried over anhydrous magnesium sulfate. The drying agent was removed, and the solvent was distilled off under reduced pressure to obtain a crude product (14.0 g). The composition of the product was found to be 2-chloro-4-fluorophenol (98.3%), 2,6-dichloro-4-fluorophenol (1.4%) and unreacted starting material (0.3%) (by glc), and production of other highly chlorinated products was not observed.

EXAMPLE 8

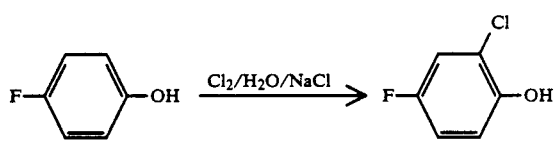

4-Fluorophenol (11.2 g, 0.10 mol) and 3.5% solution of sodium chloride (20 ml) were added to a three-necked glass flask equipped with a chlorine-gas introducing tube, and an equimolar amount of chlorine gas was introduced into the mixture at 25°-35° C. over a period of 15 minutes. After completion of the reaction, the aqueous layer and the organic layer were separated to obtain a crude product. The composition of the product was found to be 2-chloro-4-fluorophenol (93.0%), 2,6-dichloro-4-fluorophenol (6.4%) and unreacted starting material (0.6%) (by glc), and production of other highly chlorinated products was not observed.

What is claimed is:

1. A process for preparing 2-chloro-4-fluorophenol which comprises chlorinating 4-fluorophenol with a chlorinating agent selected from chroline gas and sulfuryl chloride in the presence of water in an amount sufficient to substantially dissolve the hydrogen chloride generated during the reaction.

2. A process as claimed in claim 1, wherein said chlorinating agent is chlorine gas.

3. A process as claimed in claim 1, wherein said chlorinating agent is sulfuryl chloride.

4. A process as claimed in claim 1, wherein said water is water or an aqueous solution of an inorganic salt or acid.

5. A process as claimed in claim 4, wherein said inorganic salt or acid is a compound selected from the group consisting of sodium chloride, magnesium chloride, acetic acid and hydrochloric acid.

6. A process as claimed in claim 1, wherein said chlorination is carried out in the presence of a solvent which does not take part in the chlorination.

7. A process as claimed in claim 6, wherein said solvent is selected from the group consisting of carbon tetrachloride, chloroform, dichloromethane and dichloroethane.

8. A process as claimed in claim 1, wherein said chlorination is carried out in the presence of a phase transfer catalyst.

9. A process as claimed in claim 8, wherein said phase transfer catalyst is a quaternary ammonium salt.

* * * * *